(12) United States Patent
Orishimo et al.

(10) Patent No.: US 10,988,751 B2
(45) Date of Patent: Apr. 27, 2021

(54) DIPHOSPHOMEVALONATE DECARBOXYLASE VARIANT AND METHOD FOR MANUFACTURING OLEFIN COMPOUND USING SAME

(71) Applicants: RIKEN, Wako (JP); ZEON CORPORATION, Tokyo (JP); The Yokohama Rubber Co., Ltd., Tokyo (JP)

(72) Inventors: Ryoko Orishimo, Wako (JP); Tomokazu Shirai, Wako (JP); Kazuhiro Takahashi, Tokyo (JP); Misao Hiza, Hiratsuka (JP); Yusuke Tanabe, Hiratsuka (JP)

(73) Assignees: RIKEN, Wako (JP); ZEON CORPORATION, Tokyo (JP); THE YOKOHAMA RUBBER CO., LTD., Tokyo (JP)

( * ) Notice: Subject to any disclaimer, the term of this patent is extended or adjusted under 35 U.S.C. 154(b) by 0 days.

(21) Appl. No.: 16/481,585

(22) PCT Filed: Jan. 30, 2018

(86) PCT No.: PCT/JP2018/002875
§ 371 (c)(1),
(2) Date: Jul. 29, 2019

(87) PCT Pub. No.: WO2018/143163
PCT Pub. Date: Aug. 9, 2018

(65) Prior Publication Data
US 2019/0345476 A1 Nov. 14, 2019

(30) Foreign Application Priority Data
Feb. 1, 2017 (JP) .............................. JP2017-016864

(51) Int. Cl.
| C12P 5/02 | (2006.01) |
| C12N 9/88 | (2006.01) |
| C12P 5/00 | (2006.01) |

(52) U.S. Cl.
CPC ............... *C12N 9/88* (2013.01); *C12P 5/007* (2013.01); *C12P 5/02* (2013.01); *C12Y 401/01033* (2013.01)

(58) Field of Classification Search
None
See application file for complete search history.

(56) References Cited

U.S. PATENT DOCUMENTS

| 2010/0192985 A1* | 8/2010 | Aehle ................ C11D 3/38645 134/26 |
| 2015/0037860 A1 | 2/2015 | Botes et al. |
| 2016/0160204 A1 | 6/2016 | Mazaleyrat et al. |
| 2018/0080052 A1* | 3/2018 | Lee ................ C12Y 101/01088 |

FOREIGN PATENT DOCUMENTS

| JP | 2015-501660 A | 1/2015 |
| WO | 2013-092567 A2 | 6/2013 |
| WO | 2015/004211 A2 | 1/2015 |
| WO | 2015/021045 A2 | 2/2015 |
| WO | 2017/022804 A1 | 2/2017 |

OTHER PUBLICATIONS

Weerasinghe et al., "Simulation of structural and functional properties of mevalonate diphosphate decarboxylase (MVD)", J. Mol. Model. 16:489-498, 2010 (Year: 2010).*
Zhang et al., Structure 26:1474-1485, 2018 (Year: 2018).*
Rossoni et al., Appl. Environ. Microbiol. 81:2625-2634, 2015 (Year: 2015).*
Krepkiyetal., Biochemistry 44:2671-2677, 2005 (Year: 2005).*
Aug. 6, 2019 International Preliminary Report on Patentability issued in International Patent Application No. PCT/JP2018/002875.
Gogerty, David et al., "Formation of Isobutene from 3-Hydroxy-3-Methylbutyrate by Diphosphomevalonate Decarboxylase," Applied and Environmental Microbiology, vol. 76, No. 24, pp. 8004-8010, 2010.
Orishimo et al. "Alternation of Substrate Specificity for Bio-isoprene Production," Lecture Abstract Collection for the Annual Meeting of the Japan Society for Bioscience, Biotechnology, and Agrochemistry, vol. 2016, p. 2J003 (issued on Mar. 5, 2016), and the accompanying poster (released on Mar. 28, 2016).
Apr. 24, 2018 Search Report issued in International Patent Application No. PCT/JP2018/002875.

* cited by examiner

*Primary Examiner* — David Steadman
(74) *Attorney, Agent, or Firm* — Oliff PLC

(57) ABSTRACT

A method enables olefin compound production with a high productivity, and an enzyme is used in the method. Mutations involving amino acid substitution are introduced into various sites of diphosphomevalonate decarboxylase (MVD) to prepare multiple MVD variants. Then, these variants are evaluated in terms of catalytic activity for producing an olefin compound such as isoprene, and have found as a result that the catalytic activity is improved when serine at position 153 and threonine at position 209 are each substituted with a different amino acid. In addition, the catalytic activity of the variants is further improved when glycine at position 152 is further substituted with a different amino acid.

5 Claims, 3 Drawing Sheets

Specification includes a Sequence Listing.

DIPHOSPHOMEVALONATE DECARBOXYLASE VARIANT AND METHOD FOR MANUFACTURING OLEFIN COMPOUND USING SAME

TECHNICAL FIELD

The present invention relates to a method for producing an olefin compound by using a diphosphomevalonate decarboxylase variant. In addition, the present invention relates to the variant, and a method for producing the variant. Further, the present invention also relates to a DNA encoding the variant, and a vector comprising the DNA inserted therein. Moreover, the present invention relates to a method for producing an olefin compound by using a host cell comprising the DNA or the vector introduced therein. Furthermore, the present invention also relates to an agent for promoting olefin compound production, the agent comprising the variant, the DNA, or the vector.

BACKGROUND ART

Olefin compounds such as isoprene are very useful as raw materials for various synthetic polymers such as synthetic rubbers. The compounds can be obtained by chemical methods such as fractional distillation of petroleum.

Nevertheless, even by such chemical methods, the yield is low, the production cost is high, and it takes time. Further, in consideration of the recent environmental problems, there are demands for the development of environmentally-friendly and sustainable methods for producing olefin compounds without wasting limited resources, instead of the chemical methods.

In view of such a situation, efforts have been made to produce olefin compounds by utilizing or modifying metabolic pathways of microorganisms and so forth. For example, there have been disclosed methods for producing isoprene and the like by introducing a mutation into a diphosphomevalonate decarboxylase or the like involved in the mevalonate pathway, and thereby utilizing the enzyme variant (PTLs 1 to 3).

Also, it has been attempted by the present inventors to produce isoprene and the like by introducing one or more amino acid mutations in a diphosphomevalonate decarboxylase and changing the substrate specificity of the enzyme (diphosphomevalonate decarboxylase variant) from the original 5-diphosphomevalonic acid to that for 3-hydroxy-3-methylpent-4-enotate or the like.

More specifically, the present inventors introduced mutations involving amino acid substitution into various sites of diphosphomevalonate decarboxylase, and prepared about 200 diphosphomevalonate decarboxylase variants. Then, these variants were evaluated in terms of the catalytic activity for isoprene production.

As a result, the prevent inventors have revealed that, among the many, about 200 variants, a diphosphomevalonate decarboxylase (R74HT209R) in which arginine at position 74 is substituted with histidine and threonine at position 209 is substituted with arginine has by far the highest catalytic activity for isoprene production (NPL 1).

CITATION LIST

Patent Literature

[PTL 1] International Publication No. WO2013/092567
[PTL 2] International Publication No. WO2015/004211
[PTL 3] International Publication No. WO2015/021045

Non Patent Literature

[NPL 1] ORISHIMO Ryoko et al., "Modification of Substrate Specificity of Useful Enzymes and Application to Bioisoprene Production," Lecture Abstract Collection for the Annual Meeting of the Japan Society for Bioscience, Biotechnology, and Agrochemistry, vol. 2016, p. 2J003 (issued on Mar. 5, 2016), and the accompanying poster (released on Mar. 28, 2016).

SUMMARY OF INVENTION

Technical Problem

The present invention has been made in view of the above-described problems, and an object thereof is to provide an enzyme which enables olefin compound production with a high productivity.

Solution to Problem

The present inventors conducted extensive research in order to further obtain, in addition to the above R74HT209R, a diphosphomevalonate decarboxylase variant which exhibits a high catalytic activity for isoprene production, and consequently found that a diphosphomevalonate decarboxylase (S153XT209X) in which serine at position 153 and threonine at position 209 in the diphosphomevalonate decarboxylase are each substituted with a different amino acid has a high catalytic activity for isoprene production. In particular, S153XT209X was further revealed to have about four times or higher catalytic activity than that of R74HT209R, which was previously obtained as an only variant, among the approximately 200 variants, with a very high catalytic activity for isoprene production.

Note that, in the description of the present specification, "X" as described above means a different amino acid for substitution at each site (for example, "X" of "S153X" means an amino acid other than serine, and "X" of T209X means an amino acid other than threonine).

Moreover, in the above-described S153XT209X, the present inventors further substituted glycine at position 152 with a different amino acid. As a result, it was found that the catalytic activity was further improved 1.3 times. Still more, in this triple variant (G152XS153XT209X), it was revealed that further substitution of arginine at position 74 with a different amino acid further improved the catalytic activity at most more than 3 times.

In addition, it was also found that these diphosphomevalonate decarboxylase variants exhibited high catalytic activity not only in isoprene but also in isobutene production. These findings have led to the completion of the present invention. Specifically, the present invention provides the following.

<1> A method for producing an olefin compound, the method comprising the step of reacting ATP and a compound represented by the following formula (1) in the presence of a diphosphomevalonate decarboxylase in which serine at position 153 or serine corresponding to the position, and threonine at position 209 or threonine corresponding to the position in the amino acid sequence specified in SEQ ID NO: 2 are each mutated to a different amino acid

[Chem. 1]

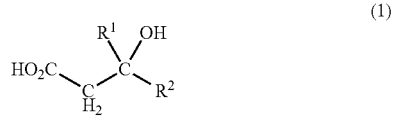

[in the formula (1), $R^1$ and $R^2$ each independently represent a hydrogen atom, an alkyl group having 1 to 10 carbon atoms, an alkenyl group having 2 to 15 carbon atoms, an aryl group having 6 to 20 carbon atoms, or a halogen atom (the alkyl group and the alkenyl group may be each independently optionally substituted with a hydroxy group and/or a carboxy group)].

<2> A method for producing an olefin compound, the method comprising the steps of:
 culturing a host cell comprising
  a DNA encoding a diphosphomevalonate decarboxylase in which serine at position 153 or serine corresponding to the position, and threonine at position 209 or threonine corresponding to the position in the amino acid sequence specified in SEQ ID NO: 2 are each mutated to a different amino acid or
  a vector comprising the DNA; and
 collecting an olefin compound produced in the host cell and/or a culture thereof.

<3> The production method according to <1> or <2>, wherein, in the diphosphomevalonate decarboxylase, the different amino acid mutated from the serine at position 153 in the amino acid sequence specified in SEQ ID NO: 2 or the serine corresponding to the position is aspartic acid or glutamic acid.

<4> The production method according to any one of <1> to <3>, wherein, in the diphosphomevalonate decarboxylase, the different amino acid mutated from the threonine at position 209 in the amino acid sequence specified in SEQ ID NO: 2 or the threonine corresponding to the position is aspartic acid.

<5> The production method according to any one of <1> to <4>, wherein the diphosphomevalonate decarboxylase is a diphosphomevalonate decarboxylase in which glycine at position 152 in the amino acid sequence specified in SEQ ID NO: 2 or glycine corresponding to the position is further mutated to a different amino acid.

<6> The production method according to <5>, wherein, in the diphosphomevalonate decarboxylase, the different amino acid mutated from the glycine at position 152 in the amino acid sequence specified in SEQ ID NO: 2 or the glycine corresponding to the position is leucine.

<7> The production method according to <5> or <6>, wherein the diphosphomevalonate decarboxylase is a diphosphomevalonate decarboxylase in which arginine at position 74 in the amino acid sequence specified in SEQ ID NO: 2 or arginine corresponding to the position is further mutated to a different amino acid.

<8> The production method according to <7>, wherein, in the diphosphomevalonate decarboxylase, the different amino acid mutated from the arginine at position 74 in the amino acid sequence specified in SEQ ID NO: 2 or the arginine corresponding to the position is tyrosine, histidine, glutamine, or asparagine.

<9> The production method according to any one of <1> to <8>, wherein the olefin compound is isoprene.

<10> The production method according to any one of <1> to <8>, wherein the olefin compound is isobutene.

<11> A method for producing a diphosphomevalonate decarboxylase having an enhanced catalytic activity for producing an olefin compound, the method comprising the step of mutating, in a diphosphomevalonate decarboxylase, each of serine at position 153 or serine corresponding to the position, and threonine at position 209 or threonine corresponding to the position in the amino acid sequence specified in SEQ ID NO: 2 to a different amino acid.

<12> The production method according to <11>, wherein, in the diphosphomevalonate decarboxylase, the different amino acid mutated from the serine at position 153 in the amino acid sequence specified in SEQ ID NO: 2 or the serine corresponding to the position is aspartic acid or glutamic acid.

<13> The production method according to <11> or <12>, wherein, in the diphosphomevalonate decarboxylase, the different amino acid mutated from the threonine at position 209 in the amino acid sequence specified in SEQ ID NO: 2 or the threonine corresponding to the position is aspartic acid.

<14> The production method according to any one of <11> to <13>, further comprising the step of, in the diphosphomevalonate decarboxylase, mutating glycine at position 152 in the amino acid sequence specified in SEQ ID NO: 2 or glycine corresponding to the position to a different amino acid.

<15> The production method according to <14>, wherein, in the diphosphomevalonate decarboxylase, the different amino acid mutated from the glycine at position 152 in the amino acid sequence specified in SEQ ID NO: 2 or the glycine corresponding to the position is leucine.

<16> The production method according to <14> or <15>, further comprising the step of, in the diphosphomevalonate decarboxylase, mutating arginine at position 74 in the amino acid sequence specified in SEQ ID NO: 2 or arginine corresponding to the position to a different amino acid.

<17> The production method according to <16>, wherein, in the diphosphomevalonate decarboxylase, the different amino acid mutated from the arginine at position 74 in the amino acid sequence specified in SEQ ID NO: 2 or the arginine corresponding to the position is tyrosine, histidine, glutamine, or asparagine.

<18> The production method according to any one of <11> to <17>, wherein the olefin compound is isoprene.

<19> The production method according to any one of <11> to <17>, wherein the olefin compound is isobutene.

<20> A diphosphomevalonate decarboxylase in which serine at position 153 or serine corresponding to the position, and threonine at position 209 or threonine corresponding to the position in the amino acid sequence specified in SEQ ID NO: 2 are each mutated to a different amino acid.

<21> The diphosphomevalonate decarboxylase according to <20>, wherein the different amino acid mutated from the serine at position 153 in the amino acid sequence specified in SEQ ID NO: 2 or the serine corresponding to the position is aspartic acid or glutamic acid.

<22> The diphosphomevalonate decarboxylase according to <20> or <21>, wherein the different amino acid mutated from the threonine at position 209 in the amino acid sequence specified in SEQ ID NO: 2 or the threonine corresponding to the position is aspartic acid.

<23> The diphosphomevalonate decarboxylase according to any one of <20> to <22>, wherein glycine at position 152 in the amino acid sequence specified in SEQ ID NO: 2 or glycine corresponding to the position is further mutated to a different amino acid.

<24> The diphosphomevalonate decarboxylase according to <23>, wherein the different amino acid mutated from the glycine at position 152 in the amino acid sequence specified in SEQ ID NO: 2 or the glycine corresponding to the position is leucine.
<25> The diphosphomevalonate decarboxylase according to <23> or <24>, wherein arginine at position 74 in the amino acid sequence specified in SEQ ID NO: 2 or arginine corresponding to the position is further mutated to a different amino acid.
<26> The diphosphomevalonate decarboxylase according to <25>, wherein the different amino acid mutated from the arginine at position 74 in the amino acid sequence specified in SEQ ID NO: 2 or the arginine corresponding to the position is selected from the group consisting of tyrosine, histidine, glutamine, asparagine, phenylalanine, serine, and alanine (preferably tyrosine, histidine, glutamine, asparagine, phenylalanine, and serine; and further preferably tyrosine, histidine, glutamine, and asparagine), or selected from the group consisting of tyrosine, histidine, glutamine, asparagine, lysine, glutamic acid, leucine, serine, and valine (preferably tyrosine, histidine, glutamine, asparagine, lysine, glutamic acid, and leucine; and further preferably tyrosine, histidine, glutamine, asparagine, and lysine).
<27> A DNA encoding the diphosphomevalonate decarboxylase according to any one of <20> to <26>.
<28> A vector comprising the DNA according to <27>.
<29> A host cell comprising the DNA according to <27> or the vector according to <28>.
<30> A method for producing a diphosphomevalonate decarboxylase variant, the method comprising the steps of: culturing the host cell according to <29>; and collecting a protein expressed in the host cell.
<31> An agent for promoting olefin compound production by reacting ATP and a compound represented by the following formula (1), the agent comprising the diphosphomevalonate decarboxylase according to any one of <20> to <26>, a DNA encoding the diphosphomevalonate decarboxylase, or a vector comprising the DNA inserted therein

[Chem. 2]

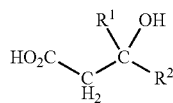

(1)

[in the formula (1), $R^1$ and $R^2$ each independently represent a hydrogen atom, an alkyl group having 1 to 10 carbon atoms, an alkenyl group having 2 to 15 carbon atoms, an aryl group having 6 to 20 carbon atoms, or a halogen atom (the alkyl group and the alkenyl group may be each independently optionally substituted with a hydroxy group and/or a carboxy group)].
<32> The agent according to <31>, wherein the olefin compound is isoprene.
<33> The agent according to <31>, wherein the olefin compound is isobutene.

Advantageous Effects of Invention

The present invention makes it possible to provide an enzyme which enables olefin compound production with a high productivity, and a method for producing an olefin compound by using the enzyme.

DESCRIPTION OF EMBODIMENTS

<Method 1 for Producing Olefin Compound>

Figure 1:
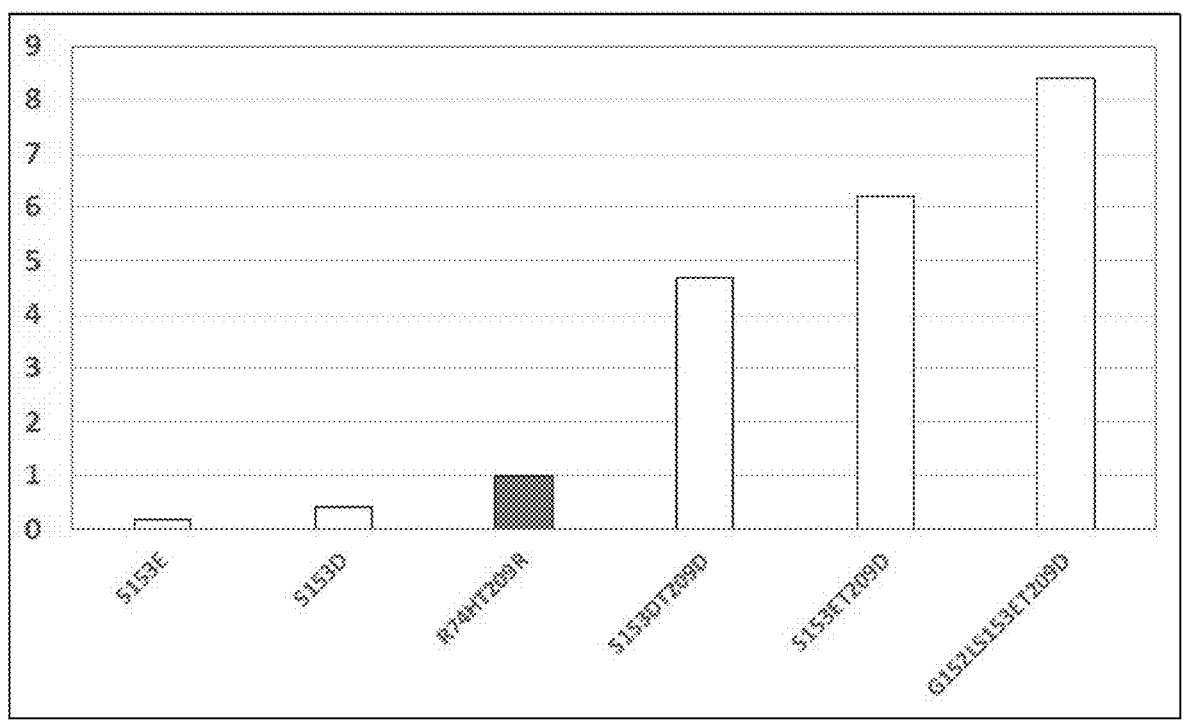
FIG. 1 is a graph about diphosphomevalonate decarboxylase variants (S153XT209X) and the like in each of which serine at position 153 and threonine at position 209 are each substituted with a different amino acid, the graph presenting results of analyzing an enzymatic activity for isoprene production using 3-hydroxy-3-methylpent-4-enotate as a substrate. Note that the vertical axis indicates an amount of isoprene produced by each amino acid variant, the amount being expressed as a relative value calculated by using the amount in a diphosphomevalonate decarboxylase variant (R74HT209R) in which arginine at position 74 and threonine at position 209 are substituted with histidine and arginine, respectively as a reference (1). Then, in the graph, "S153E" and others each indicate a diphosphomevalonate decarboxylase variant where the number indicates a position (such as position 153) into which a mutation involving amino acid substitution is introduced in the enzyme, an alphabet to the left of the number indicates an amino acid prior to the substitution (such as S/serine), and an alphabet to the right of the number indicates an amino acid after the substitution (such as E/glutamic acid).

As described in Examples later, it was found that substituting serine at position 153 and threonine at position 209 of a diphosphomevalonate decarboxylase with different amino acids improves a catalytic activity of promoting the following reaction of producing an olefin compound (also referred to as "catalytic activity for producing an olefin compound").

[Chem. 3]

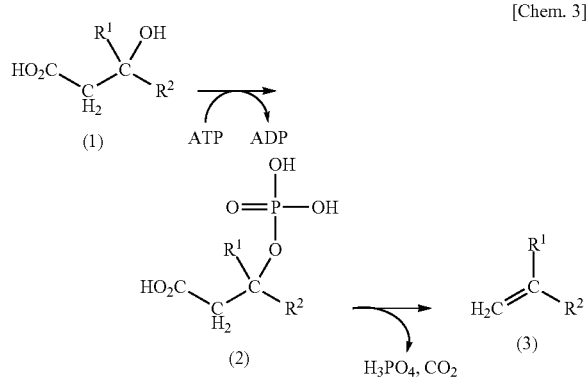

Thus, the present invention provides a method for producing an olefin compound, the method comprising the step of reacting ATP (adenosine triphosphate) and a compound represented by the above formula (1) in the presence of a diphosphomevalonate decarboxylase in which serine at position 153 or serine corresponding to the position (hereinafter, also referred to simply as "serine at position 153"), and threonine at position 209 or threonine corresponding to the position (hereinafter, also referred to simply as "threonine at position 209") in the amino acid sequence specified in SEQ ID NO: 2 are each mutated to a different amino acid (hereinafter, such a diphosphomevalonate decarboxylase is also referred to as "diphosphomevalonate decarboxylase variant").

In the present invention, the term "olefin compound" means a hydrocarbon compound having at least one carbon-carbon double bond, and may have a substituent such as a hydroxy group and/or a carboxy group, and an atom such as a halogen atom introduced in the compound. Examples of such a compound include: monoolefin compounds such as isobutene, ethene, propene, 2-methyl-1-butene, isoprenol, and 3-hydroxy-3-methyl-4-pentenoic acid; and diolefin compounds such as conjugated diene compounds including isoprene, butadiene (1,3-butadiene), piperylene, 2,3-dimethylbutadiene, 1,3-hexadiene, 2-methyl-1,3-pentadiene, chloroprene, and 3-methyl-2,4-pentadienoic acid.

In the compound represented by the following formula (1) which serves as a raw material for producing the olefin compound in the present invention, $R^1$ and $R^2$ are not particularly limited, and each independently represent a hydrogen atom, an alkyl group having 1 to 10 carbon atoms, an alkenyl group having 2 to 15 carbon atoms, an aryl group having 6 to 20 carbon atoms, or a halogen atom (the alkyl group and the alkenyl group may be each independently optionally substituted with a hydroxy group and/or a carboxy group).

[Chem. 4]

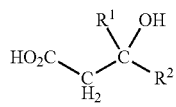

(1)

Moreover, in the present invention, in the case where a conjugated diene compound is produced, a compound represented by the following formula (4) is preferably used as a more specific embodiment of the compound represented by the formula (1), as represented by the following reaction equation.

[Chem. 5]

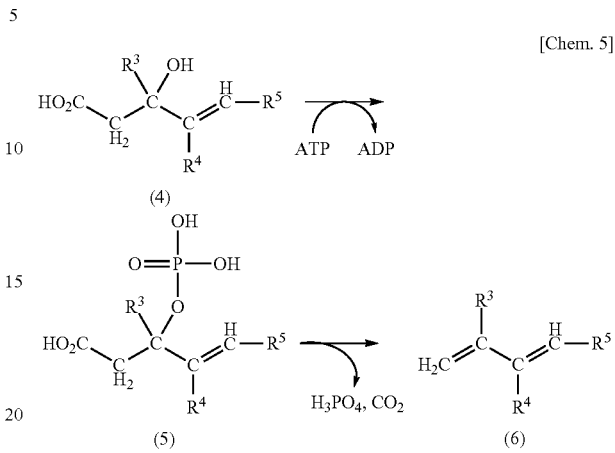

In the compound represented by the formula (4), $R^3$, $R^4$, and $R^5$ are not particularly limited, and each independently represent a hydrogen atom or a substituent selected from the group consisting of an alkyl group having 1 to 10 carbon atoms, a halogen atom, an alkenyl group having 2 to 15 carbon atoms, and an aryl group having 6 to 20 carbon atoms.

In addition, in the present invention, examples of the alkyl group having 1 to 10 carbon atoms include a methyl group, an ethyl group, an n-propyl group, an i-propyl group, an n-butyl group, an i-butyl group, a s-butyl group, a t-butyl group, an n-pentyl group, an n-hexyl group, a cyclopropyl group, a cyclopentyl group, a cyclohexyl group, an n-heptyl group, an n-octyl group, an n-decyl group, a (cyclohexyl) methyl group, a (1-methylcyclohexyl)methyl group, a (1-methylcyclopentyl)methyl group, and a (1-ethylcyclohexyl)methyl group. Moreover, examples of the alkenyl group having 2 to 15 carbon atoms include a vinyl group, a 1-propenyl group, a 2-propenyl group, a 2-methyl-2-propenyl group, a 3-butenyl group, a 5-hexenyl group, and a 7-octenyl group. Examples of the aryl group having 6 to 20 carbon atoms include a phenyl group, a 1-naphthyl group, a 2-naphthyl group, an acenaphthyl group, a phenanthryl group, and an anthryl group. Further, the halogen atom represents a chlorine atom, a fluorine atom, a bromine atom, or an iodine atom.

Such compounds represented by the formula (1) can be purchased as commercially available products as described in Examples later. Alternatively, those skilled in the art can also synthesize the compounds as appropriate with reference to known synthesis methods (for example, the method described in Tetrahedron Letters, 1988, vol. 20, iss. 15, pp. 1763 to 1766).

In the presence of the diphosphomevalonate decarboxylase variant to be described later, the reaction conditions for the ATP and the compound represented by the formula (1) may be any conditions under which the reaction is promoted and an olefin compound is produced. Those skilled in the art can adjust and set the composition of a reaction liquid, the pH of the reaction liquid, the reaction temperature, the reaction time, and so forth as appropriate.

For example, the reaction liquid to which the diphosphomevalonate decarboxylase variant, the compound represented by the formula (1) serving as the substrate of the variant, and ATP are added only has to contain magnesium ions, which serve as a cofactor of the diphosphomevalonate decarboxylase, in an amount of normally 1 to 50 mM, and preferably 5 to 20 mM. The other composition and pH are not particularly limited as described above, as long as the reaction is not inhibited. The reaction liquid is preferably a buffer having a pH of 7 to 8, and is more preferably a Tris-HCl buffer having a pH of 7 to 8.

Moreover, the reaction temperature is not particularly limited, either, as long as the reaction is not inhibited. Nevertheless, the reaction temperature is normally 20 to 40° C., and preferably 25 to 37° C. Further, the reaction time may be any period of time in which an olefin compound can be produced, and is not particularly limited. The reaction time is normally 30 minutes to 7 days, and preferably 12 hours to 2 days.

Furthermore, olefin compounds produced under such conditions generally tend to vaporize. Hence, the olefin compounds can be collected by known volatile gas recovery and purification methods. The collection method is gas stripping, fractional distillation, adsorption, desorption, pervaporation, heat or vacuum desorption of isoprene from a solid phase to which the isoprene is adsorbed, extraction with a solvent, chromatography (for example, gas chromatography), or the like. Moreover, even in the case where the produced olefin compound is a liquid, the olefin compound can be collected by utilizing known recovery and purification methods (such as distillation and chromatography) as appropriate. Further, these methods may be each performed alone, or may be performed in an appropriate combination in multiple stages.

<Method 2 for Producing Olefin Compound>

Additionally, as described in Examples later, culturing a host cell transformed to express a diphosphomevalonate decarboxylase in which serine at position 153 or serine corresponding to the position, and threonine at position 209 or threonine corresponding to the position in the amino acid sequence specified in SEQ ID NO: 2 are each mutated to a different amino acid enables olefin compound production with a high productivity. Thus, the present invention also provides a method for producing an olefin compound, the method comprising the steps of: culturing a host cell comprising a vector or a DNA encoding a diphosphomevalonate decarboxylase variant to be described later; and collecting an olefin compound produced in the host cell and/or a culture thereof.

Although the culturing conditions of the host cell will be described later, a medium therefor is preferably supplemented with the compound represented by the formula (1) which serves as a substrate of the diphosphomevalonate decarboxylase and magnesium ions which serve as a cofactor, and more preferably supplemented with all of these compounds. In addition, the culturing temperature can be designed and changed as appropriate depending on the type of the host cell used, and is normally 20 to 40° C., and preferably 25 to 37° C.

Moreover, in the present invention, the "culture" refers to a medium containing the proliferated host cell, a secretion of the host cell, and a metabolite of the host cell, and the like, which are obtained by culturing the host cell in the medium. The culture also includes dilutions and concentrates of these.

Collection of the olefin compound from such a host cell and/or culture is not particularly limited, but may be carried out by using the above-described known recovery and purification methods. Further, the collection timing is adjusted as appropriate depending on the type of the host cell used, and just should be a timing as of which an olefin compound can be produced. A time period as of the collection is normally 30 minutes to 7 days, and preferably 12 hours to 2 days.

<Diphosphomevalonate Decarboxylase Variant>

Next, description is given of the diphosphomevalonate decarboxylase variant used in the above-described method for producing an olefin compound of the present invention. The "diphosphomevalonate decarboxylase" in the present invention is also referred to as MVD, and is an enzyme registered under EC number: 4.1.1.33. This enzyme is one type of carboxy-lyase which catalyzes the following reaction of producing isopentenyl diphosphate, ADP, phosphoric acid, and carbon dioxide from 5-diphosphomevalonic acid and ATP.

[Chem. 6]

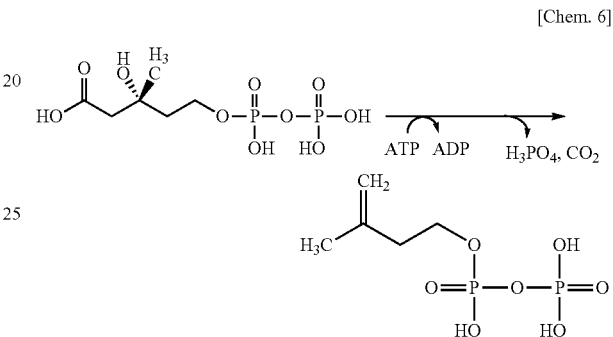

In the present invention, the diphosphomevalonate decarboxylase into which a mutation to be described later is to be introduced is not particularly limited, and those derived from various organisms can be used. Examples of such an enzyme include MVD derived from *Saccharomyces cerevisiae* (a protein comprising the amino acid sequence specified in SEQ ID NO: 2), MVD derived from *Saccharomyces cerevisiae* (strain YJM7) (a protein specified by UniProt Accession No: A6ZSB7), MVD derived from *Saccharomyces cerevisiae* (strain RM11-1a) (a protein specified by UniProt Accession No: B3LPK0), MVD derived from *Candida dubliniensis* (a protein specified by UniProt Accession No: B9W6G7), MVD derived from *Pichia pastoris* (a protein specified by UniProt Accession No: C4QX63), MVD derived from *Schizosaccharomyces pombe* (a protein specified by UniProt Accession No: O139363), MVD derived from *Ashbya gossypii* (a protein specified by UniProt Accession No: Q751D8), MVD derived from *Debaryomyces hanseni* (a protein specified by UniProt Accession No: Q6BY07), MVD derived from *Dictyostellum discoideum* (a protein specified by UniProt Accession No: Q54YQ9), MVD derived from *Aspergillus oryzae* (a protein specified by UniProt Accession No: Q2UGF4), MVD derived from *Encephalitozoon cuniculi*) (a protein specified by UniProt Accession No: Q8SRR7), MVD derived from *Phaeodactylum tricornutum* (a protein specified by UniProt Accession No: B7S422), MVD derived from Para rubber tree (*Hevea brasiliensis*) (a protein specified by UniProt Accession No: A9ZN03), MVD derived from tobacco (*Nicotiana langsdorffii* x *Nicotiana sanderae*) (a protein specified by UniProt Accession No: B3F8H5), MVD derived from *Arnebia euchroma* (a protein specified by UniProt Accession No: Q09RL4), MVD derived from *Japonica* rice (*Oryza sativa* subsp. *Japonica*) (a protein specified by UniProt Accession No: Q6ETS8), MVD derived from *Arabidopsis thaliana* (a protein specified by UniProt Accession No: QBLB37), MVD derived from tomato (*Solanum lycopersicum*) (a protein specified by UniProt Accession No: ABWBX7), MVD derived from silkworm (*Bombyx mori*) (a protein specified by UniProt Accession No: A5A7A2), MVD derived from zebrafish (*Danio rerio*) (a protein specified by UniProt Accession No: Q5U403), MVD derived from mouse (*Mus musculus*) (a protein specified by UniProt Accession No: Q99JF5 or Q3UYC1), MVD derived from brown rat (*Rattus norvegicus*) (a protein specified by UniProt Accession No: Q62967), MVD derived from cattle (*Bos taurus*) (a protein specified by UniProt Accession No: Q0P570), and MVD derived from human (*Homo sapiens*) (a protein specified by UniProt Accession No: P53602). Among these, preferable are MVDs derived from *Saccharomyces cerevisiae*, and more preferable is the 26 protein comprising the amino acid sequence specified in SEQ ID NO: 2. Meanwhile, it should be understood that, in the natural world, the amino acid sequence of a protein may vary due to a mutation in the nucleotide sequence.

Further, the "diphosphomevalonate decarboxylase" of the present invention may have a mutation artificially introduced therein, other than the serine at position 153 and the threonine at position 209 in the amino acid sequence specified in SEQ ID NO: 2. To be more specific, the "diphosphomevalonate decarboxylase" of the present invention also includes "a protein comprising an amino acid sequence of diphosphomevalonate decarboxylase (such as the amino acid sequence specified in SEQ ID NO: 2) in which one or multiple amino acids are substituted, deleted, added, and/or inserted except for the amino acids at position 153 and position 209". Here, the term "multiple" is not particularly limited, but refers to normally 2 to 80, preferably 2 to 40, more preferably 2 to 20, and even more preferably 2 to 10 (for example, 2 to 8, 2 to 4, or 2).

Moreover, in the "diphosphomevalonate decarboxylase" of the present invention, a mutation of an amino acid in a position other than the serine at position 153 or the serine corresponding to the position, and the threonine at position 209 or the threonine corresponding to the position in the amino acid sequence specified in SEQ ID NO: 2 is not particularly limited, as long as the resultant has a catalytic activity for producing an olefin compound. Nevertheless, as described in Examples later, from the viewpoint that the activity tends to be higher, it is preferable that glycine at position 152 in the amino acid sequence specified in SEQ ID NO: 2 or glycine corresponding to the position (hereinafter also simply referred to as "glycine at position 152") be mutated to a different amino acid, and it is more preferable that arginine at position 74 in the amino acid sequence specified in SEQ ID NO: 2 or arginine corresponding to the position (hereinafter also simply referred to as "arginine at position 74") be also mutated to a different amino acid.

In the present invention, the "different amino acid" mutated from the serine at position 153 in the amino acid sequence specified in SEQ ID NO: 2 or the serine corresponding to the position is not particularly limited, as long as the different amino acid is an amino acid other than serine. Nevertheless, as described in Examples later, from the viewpoint that a high catalytic activity is readily exhibited in the olefin compound production, preferable is aspartic acid or glutamic acid, and more preferable is glutamic acid.

In addition, in the present invention, the "different amino acid" mutated from the threonine at position 209 in the amino acid sequence specified in SEQ ID NO: 2 or the threonine corresponding to the position is not particularly limited, as long as the different amino acid is an amino acid other than threonine. Nevertheless, as described in Examples later, from the viewpoint that a high catalytic activity is readily exhibited in the olefin compound production, preferable is aspartic acid.

Moreover, in the present invention, the "different amino acid" mutated from the glycine at position 152 in the amino acid sequence specified in SEQ ID NO: 2 or the glycine corresponding to the position is not particularly limited, as long as the different amino acid is an amino acid other than glycine. Nevertheless, as described in Examples later, from the viewpoint that a high catalytic activity is readily exhibited in the olefin compound production, preferable is leucine.

Moreover, in the present invention, the "different amino acid" mutated from the arginine at position 74 in the amino acid sequence specified in SEQ ID NO: 2 or the arginine corresponding to the position is not particularly limited, as long as the different amino acid is an amino acid other than arginine. Nevertheless, as described in Examples later, from the viewpoint that a high catalytic activity is readily exhibited in the olefin compound production, the different amino acid is preferably selected from the group consisting of tyrosine, histidine, glutamine, asparagine, phenylalanine, serine, alanine, lysine, glutamic acid, valine, and leucine, and more preferably selected from the group consisting of tyrosine, histidine, glutamine, and asparagine. In addition, from the viewpoint that a high catalytic activity is readily exhibited in the isoprene production, the different amino acid is selected from the group consisting of preferably tyrosine, histidine, glutamine, asparagine, phenylalanine, serine, and alanine (more preferably tyrosine, histidine, glutamine, asparagine, phenylalanine, and serine; and further preferably tyrosine, histidine, glutamine, and asparagine), for example. In addition, from the viewpoint that a high catalytic activity is readily exhibited in the isobutene production, the different amino acid is selected from the group consisting of preferably tyrosine, histidine, glutamine, asparagine, lysine, glutamic acid, leucine, serine, and valine (more preferably tyrosine, histidine, glutamine, asparagine, lysine, glutamic acid, and leucine; and further preferably tyrosine, histidine, glutamine, asparagine, and lysine), for example.

Note that, in the present invention, a "corresponding position" is defined as follows. Specifically, when the amino acid sequence specified in SEQ ID NO: 2 and another amino acid sequence of MVD or the like derived from a different strain are aligned with each other by utilizing nucleotide and amino acid sequence analysis software (such as GENETYX-MAC or Sequencher) or BLAST (blast.ncbi.nlm.nih.gov/Blast.cgi), the "corresponding position" is a position in the other amino acid sequence located at the same place as the position 153, the position 209, the position 152, or the position 74 in the amino acid sequence specified in SEQ ID NO: 2.

Meanwhile, the "wild-type diphosphomevalonate decarboxylase" is a diphosphomevalonate decarboxylase before the introduction of the mutations into the serine at position 153 and the threonine at position 209 in the amino acid sequence specified in SEQ ID NO: 2 and the aforementioned artificial mutation. Examples of the wild type include diphosphomevalonate decarboxylases derived from various organisms such as *Saccharomyces cerevisiae* and naturally-occurring variants thereof, as described above.

Furthermore, whether or not a diphosphomevalonate decarboxylase variant has a catalytic activity for producing an olefin compound can be determined, for example, by directly measuring the amount of olefin compound by gas chromatography-mass spectrometry (GC-MS), as described in Examples later. Further, whether or not the diphosphomevalonate decarboxylase variant has a higher catalytic activity for producing an olefin compound than the wild-type diphosphomevalonate decarboxylase can be also determined by comparing the amounts measured for these two types of diphosphomevalonate decarboxylase.

In the present invention, the catalytic activity for producing an olefin compound of the diphosphomevalonate decarboxylase variant in comparison with the catalytic activity of the wild-type diphosphomevalonate decarboxylase is preferably 10 times or more (for example, 20 times or more, 30 times or more, or 40 times or more), more preferably 50 times or more (for example, 60 times or more, 70 times or more, 80 times or more, or 90 times or more), further preferably 100 times or more (for example, 200 times or more, 300 times or more, or 400 times or more), much more preferably 500 times or more (for example, 600 times or more, 700 times or more, 800 times or more, or 900 times or more), still more preferably 1000 times or more (for example, 1100 times or more, 1200 times or more, 1300 times or more, or 1400 times or more), and particularly preferably 1500 times or more (for example, 1600 times or more, 1700 times or more, 1800 times or more, or 1900 times or more).

Further, to the diphosphomevalonate decarboxylase variant, a different compound may be added directly or indirectly. This addition is not particularly limited, and the compound may be added at a gene level, or may be chemically added. Moreover, the site of the addition is not particularly limited, either. The site may be any one or both of an amino terminus (hereinafter also referred to as "N-terminus") and a carboxyl terminus (hereinafter also referred to as "C-terminus") of the diphosphomevalonate decarboxylase variant. The addition at a gene level is accomplished by using a DNA encoding the diphosphomevalonate decarboxylase variant to which a DNA encoding a different protein is added with their reading frames alighted with each other. The "different protein" added in this manner is not particularly limited. For the purpose of facilitating the purification of the diphosphomevalonate decarboxylase variant, a tag protein for purification is suitably used such as a polyhistidine (His-) tag protein, a FLAG-tag protein (registered trademark, Sigma-Aldrich Co. LLC.), or glutathione-S-transferase (GST). Meanwhile, for the purpose of facilitating the detection of the diphosphomevalonate decarboxylase variant, a tag protein for detection is suitably used such as a fluorescent protein, namely, GFP or a chemiluminescent protein, namely, luciferase. The chemical addition may be covalent bonding, or may be non-covalent bonding. The "covalent bonding" is not particularly limited, and examples thereof include an amide bond between an amino group and a carboxyl group, an alkylamine bond between an amino group and an alkyl halide group, a disulfide bond between thiols, and a thioether bond between a thiol group and a maleimide group or an alkyl halide group. An example of the "non-covalent bonding" is a bonding between biotin and avidin. Further, as the "different compound" chemically added as described above, for example, a fluorescent dye such as Cy3 or rhodamine is preferably used for the purpose of facilitating the detection of the diphosphomevalonate decarboxylase variant.

In addition, the diphosphomevalonate decarboxylase variant of the present invention may be used in mixture with other components. The other components are not particularly limited, and examples thereof include sterile water, a saline, a vegetable oil, a surfactant, a lipid, a solubilizer, a buffer, a protease inhibitor, and a preservative.

<DNA Encoding Diphosphomevalonate Decarboxylase Variant, and Vector Having the DNA>

Next, a DNA encoding the diphosphomevalonate decarboxylase variant and so forth are described. Introducing such a DNA into a host cell leads to transformation of the host cell such that the cell can produce the diphosphomevalonate decarboxylase variant in the cell, and consequently produce an olefin compound.

The DNA of the present invention may be a naturally-occurring DNA in which a mutation is artificially introduced, or may be a DNA comprising an artificially designed nucleotide sequence. Further, the form of DNA is not particularly limited, and includes, besides a cDNA, a genomic DNA and a chemically synthesized DNA. These DNAs can be prepared by utilizing means usually used by those skilled in the art. The genomic DNA can be prepared, for example, by extracting a genomic DNA from *Saccharomyces cerevisiae* or the like, constructing a genomic library (a plasmid, phage, cosmid, BAC, PAC, or the like can be utilized as the vector), and plating the library, followed by colony hybridization or plaque hybridization using a probe prepared based on the nucleotide sequence of the diphosphomevalonate decarboxylase gene (for example, the nucleotide sequence specified in SEQ ID NO: 1). Alternatively, the genomic DNA can also be prepared by producing a primer specific to the diphosphomevalonate decarboxylase gene, followed by PCR utilizing the primer. Meanwhile, the cDNA can be prepared, for example, by synthesizing a cDNA based on an mRNA extracted from *Saccharomyces cerevisiae*, inserting the cDNA into a vector such as AZAP to construct a cDNA library, and plating the library, followed by PCR or either one of the colony hybridization and plaque hybridization in the same manner as above.

Those skilled in the art can then introduce into the thus prepared DNA a mutation to substitute each of the serine at position 153, the threonine at position 209, and so forth in the amino acid sequence specified in SEQ ID NO: 2 in the diphosphomevalonate decarboxylase with a 26 different amino acid by utilizing a known method of site-directed mutagenesis. Examples of the site-directed mutagenesis include the Kunkel method (Kunkel, T. A., Proc Natl Acad Sci USA, 1985, vol. 82, No. 2, pp. 488 to 492), and SOE (splicing-by-overlap-extention)-PCR (Ho, S. N., Hunt, H. D., Horton, R. M., Pullen, J. K., and Pease, L. R., Gene, 1989, vol. 77, pp. 51 to 59).

Moreover, those skilled in the art can also artificially design a nucleotide sequence encoding a diphosphomevalonate decarboxylase protein in which the serine at position 153 and the threonine at position 209 are each substituted with a different amino acid, and chemically synthesize the DNA of the present invention by using an automatic nucleic acid synthesizer based on information on the sequence.

According to these methods, an amino acid(s) at positions (for example, at position 152 in the amino acid sequence specified in SEQ ID NO: 2 and at position 74 in the amino acid sequence specified in SEQ ID NO: 2) other than the serine at position 153 and the threonine at position 209 in the diphosphomevalonate decarboxylase can each be also substituted with another amino acid(s), as a matter of course.

Further, from the viewpoint that the efficiency of expressing a diphosphomevalonate decarboxylase variant encoded by a DNA is further enhanced in the host cell to be described later, the DNA of the present invention can also be in the form of a DNA encoding a diphosphomevalonate decarboxylase variant and having codons optimized for the type of the host cell.

Additionally, the present invention also provides a vector comprising the above-described DNA inserted therein so that the DNA can be replicated in the host cell.

In the present invention, the "vector" can be constructed basically as a self-replicating vector, that is, for example, a plasmid which exists as an extrachromosomal element, and which can be replicated independently of the replication of the chromosome. Alternatively, the vector may be one which is incorporated into a genome of a host cell when introduced into the host cell, and is replicated together with the chromosome of the host cell.

Examples of such a vector include plasmids and phage DNAs. Moreover, the plasmids include *Escherichia coli*-derived plasmids (such as pBR322, pBR325, pUC118, pUC119, pUC18, and pUC19), yeast-derived plasmids (such as YEpl3, YEp24, and YCp50), and *Bacillus subtilis*-derived plasmids (such as pUB110 and pTP5). The phageDNAs include lambda phages (such as Charon4A, Charon21A, EMBL3, EMBL4, λgt10, λgt11, and AZAP). Further, as the vector of the present invention, it is also possible to use: insect viral vectors such as baculoviridae if the host cell is derived from an insect; T-DNA and the like if the host cell is derived from a plant; and animal viral vectors such as retroviruses and adenoviral vectors if the host cell is derived from an animal. In addition, as the procedure and the method for constructing the vector of the present invention, those conventionally employed in the field of genetic engineering can be employed. For example, to insert the DNA of the present invention into the vector, adopted is a method in which the purified DNA is first digested with a restriction enzyme to cut the DNA into fragments, and a fragments is then inserted into a restriction site or multiple cloning site of an appropriate vector, and bonded to the vector, or other similar methods.

Moreover, the vector of the present invention may be in the form of an expression vector comprising a DNA in such a manner that the diphosphomevalonate decarboxylase variant encoded by the DNA can be expressed in the host cell. Desirably, in order for the "expression vector" according to the present invention to express the diphosphomevalonate decarboxylase variant after being introduced into a host cell, the "expression vector" comprises, in addition to the DNA, a DNA sequence for regulating the expression, a gene marker for selecting the transformed host cell, and the like. The DNA sequences for regulating the expression include a promoter, an enhancer, a splicing signal, a poly-A addition signal, a ribosome binding sequence (SD sequence), a terminator, and the like. The promoter is not particularly limited, as long as the promoter can exhibit transcriptional activity in the host cell. The promoter can be obtained as a DNA sequence for regulating the expression of a gene encoding a protein which is either homologous or heterologous to the host cell. Additionally, the expression vector may comprise a DNA sequence for inducing the expression, in addition to the DNA sequence for regulating the expression. In a case where the host cell is a bacterium, the DNA sequence for inducing the expression may be a lactose operon capable of inducing the expression of a gene, which is located downstream, by addition of isopropyl-β-D-thiogalactopyranoside (IPTG). In the present invention, the gene marker may be selected as appropriate depending on the method for selecting the transformed host cell. For example, it is possible to utilize a gene encoding drug resistance, or a gene complementing the auxotrophy.

Further, the DNA or the vector of the present invention may be used in mixture with other components. The other components are not particularly limited, and examples thereof include sterile water, a saline, a vegetable oil, a surfactant, a lipid, a solubilizer, a buffer, a DNase inhibitor, and a preservative.

<Agent for Promoting Olefin Compound Production>

As described above, the use of the diphosphomevalonate decarboxylase variant, the DNA encoding the variant, or the vector comprising the DNA inserted therein makes it possible to promote olefin compound production by reacting ATP and a compound represented by the following formula (1). Thus, the present invention also provides an agent for promoting olefin compound production by reacting ATP and a compound represented by the following formula (1), the agent comprising a diphosphomevalonate decarboxylase in which at least serine at position 153 or serine corresponding to the position, and threonine at position 209 or threonine corresponding to the position in the amino acid sequence specified in SEQ ID NO: 2 are each mutated to a different amino acid, a DNA encoding the diphosphomevalonate decarboxylase, or a vector comprising the DNA inserted therein,

[Chem. 7]

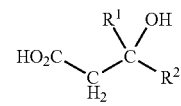

(1)

[in the formula (1), $R^1$ and $R^2$ each independently represent a hydrogen atom, an alkyl group having 1 to 10 carbon atoms, an alkenyl group having 2 to 15 carbon atoms, an aryl group having 6 to 20 carbon atoms, or a halogen atom (the alkyl group and the alkenyl group may be each independently optionally substituted with a hydroxy group and/or a carboxy group)].

Such an agent only has to comprise the above-described diphosphomevalonate decarboxylase variant or the like, and may be used in mixture with other components. The other components are not particularly limited, and examples thereof include sterile water, a saline, a vegetable oil, a surfactant, a lipid, a solubilizer, a buffer, a protease inhibitor, a DNase inhibitor, and a preservative.

In addition, the present invention can also provide a kit comprising such an agent. The kit of the present invention may comprise the agent in the form of a later-described host cell which is transformed to comprise the DNA or the like of the present invention introduced therein. Further, in addition to such an agent, the kit of the present invention may comprise a compound represented by the formula (1), a host cell for introducing the DNA or the like of the present invention, a medium for culturing the host cell, an instruction for use of them, and so forth. Moreover, the instruction for use is an instruction for utilizing the agent of the present invention and so forth in the above-described method for producing an olefin compound. The instruction may comprise, for example, experimental techniques and experimental conditions for the production methods of the present invention, and information on the agent of the present invention and so forth (for example, information such as a vector map indicating the nucleotide sequence and the like of the vector, sequence information of the diphosphomevalonate decarboxylase variant, information on the origin and nature of the host cell, culturing conditions of the host cell, and so forth).

<Host Cell Comprising DNA Encoding Diphosphomevalonate Decarboxylase Variant, Etc.>

Next, the host cell comprising the DNA or the vector of the present invention is described. The use of the host cell transformed by introducing the aforementioned DNA or vector therein makes it possible to produce the diphosphomevalonate decarboxylase variant, and consequently makes it possible to produce an olefin compound, as well.

The host cell into which the DNA or the vector of the present invention is to be introduced is not particularly limited, and examples thereof include microorganisms (such as *Escherichia coli, Saccharomyces cerevisiae, Schizosaccharomyces pombe, Bacillus subtilis,* actinobacteria, and filamentous fungi), plant cells, insect cells, and animal cells. From the viewpoints of a high proliferation exhibited in a short time on a relatively inexpensive medium and consequent contribution to olefin compound production with a high productivity, microorganisms are preferably utilized as the host cell, and *Escherichia coli* is more preferably utilized.

In addition, the DNA or the vector of the present invention can be also introduced according to the methods conventionally employed in this field. Examples of the introduction methods into microorganisms such as *Escherichia coli* include a heat shock method, an electroporation method, a spheroplast method, and a lithium acetate method. The introduction methods into plant cells include a method using *Agrobacterium* and a particle gun method. The introduction methods into insect cells include a method using Baculoviridae and an electroporation method. The introduction methods into animal cells include a calcium phosphate method, a lipofection method, and an electroporation method.

The DNA or the like introduced in the host cell as described above may be retained in the host cell by being randomly inserted in the genomic DNA, or may be retained by homologous recombination. Meanwhile, in the case of the vector, it can be replicated and retained as an extragenomic DNA element.

<Method for Producing Diphosphomevalonate Decarboxylase Variant>

As described in Examples later, culturing a host cell comprising the DNA or the like of the present invention introduced therein makes it possible to produce a diphosphomevalonate decarboxylase variant in the host 6 cell. Thus, the present invention can also provide a method for producing a diphosphomevalonate decarboxylase variant, the method comprising the steps of: culturing the host cell; and collecting a protein expressed in the host cell.

In the present invention, the conditions for "culturing the host cell" may be any conditions under which the host cell can produce the diphosphomevalonate decarboxylase variant. Those skilled in the art can adjust and set the temperature, whether to add air or not, oxygen concentration, carbon dioxide concentration, pH of the medium, culturing temperature, culturing time, humidity, and so forth as appropriate in accordance with the type of the host cell, the medium used, and the like.

The medium just has to contain what the host cell can assimilate. Examples of the content include a carbon source, a nitrogen source, a sulfur source, mineral salts, metals, peptones, yeast extract, meat extract, casein hydrolysate, serum, and the like. Moreover, such a medium may be supplemented with, for example, IPTG for inducing the expression of the DNA encoding the diphosphomevalonate decarboxylase variant, an antibiotic (for example, ampicillin) corresponding to the drug resistance gene which can be encoded by the vector according to the present invention, or a nutrient (for example, arginine or histidine) corresponding to the gene complementing the auxotrophy which can be encoded by the vector according to the present invention.

Moreover, examples of the method for "collecting a protein expressed in the host cell" from the host cell cultured as described above include methods involving: recovering the host cell from the medium by filtration, centrifugation, or the like; subjecting the recovered host cell to a treatment such as cytolysis, grinding, or pressurization crushing; and further purifying and concentrating a protein expressed in the host cell by solvent precipitation such as ultrafiltration treatment, salting-out, or ammonium sulfate precipitation, chromatography (for example, gel chromatography, ion exchange chromatography, or affinity chromatography), or the like. Further, in the case where the aforementioned purification tag protein is added to the diphosphomevalonate decarboxylase variant, the purification and collection are also possible using a substrate to which the tag protein can be adsorbed. Furthermore, these purification and concentration methods may be performed alone, or may be performed in an appropriate combination in multiple stages.

Alternatively, the diphosphomevalonate decarboxylase variant can also be produced not only by the above biological synthesis, but also by using the DNA or the like of the present invention and a cell-free protein synthesis system. The cell-free protein synthesis system is not particularly limited, and examples thereof include synthesis systems derived from wheat germ, *Escherichia coli*, rabbit reticulocyte, or insect cells. Further, those skilled in the art can also chemically synthesize the diphosphomevalonate decarboxylase variant by using a commercially-available peptide synthesizer or the like.

Moreover, the present invention can also provide a method for producing a diphosphomevalonate decarboxylase having an enhanced catalytic activity for producing an olefin compound, the method comprising the step of mutating at least serine at position 153 or serine corresponding to the position, and threonine at position 209 or threonine corresponding to the position in the amino acid sequence specified in SEQ ID NO: 2 in a diphosphomevalonate decarboxylase to a different amino acid.

The "diphosphomevalonate decarboxylase having an enhanced catalytic activity for producing an olefin compound" means a diphosphomevalonate decarboxylase having a higher catalytic activity for producing an olefin compound as a result of introducing mutations into the serine at position 153, the threonine at position 209, and the like in the diphosphomevalonate decarboxylase before the introduction. The latter diphosphomevalonate decarboxylase as a comparison target is normally the 6 diphosphomevalonate decarboxylases derived from various organisms such as *Saccharomyces cerevisiae*, and naturally-occurring variants thereof.

The "mutation to a different amino acid" in the diphosphomevalonate decarboxylase can be introduced by modifying the encoding DNA. The "DNA modification" can be performed as appropriate by employing a method known to those skilled in the art as described above, for example, the site-directed mutagenesis or the DNA chemical synthesis method based on modified sequence information. Moreover, the "mutation to a different amino acid" can also be introduced by employing the peptide chemical synthesis method as described above.

Further, whether or not the catalytic activity for producing an olefin compound is enhanced by such mutation introduction can be evaluated by the GC-MS analysis or the like as described above.

EXAMPLES

<Preparation and Evaluation of Diphosphomevalonate Decarboxylase Variants>

To achieve olefin compound production with a high productivity, the present inventors arrived at an idea of producing isoprene or the like via a reaction as represented by the following equation, by introducing a mutation into an amino acid of diphosphomevalonate decarboxylase (hereinafter also referred to as "MVD"), and changing the substrate specificity of the enzyme (diphosphomevalonate decarboxylase variant) from the original 5-diphosphomevalonic acid to that for 3-hydroxy-3-methylpent-4-enotate or the like.

[Chem. 8]

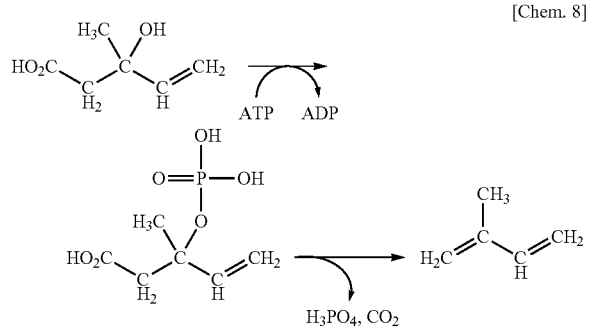

To this end, the present inventors adopted the following methods and others to introduce a mutation involving amino acid substitution into each of various sites of diphosphomevalonate decarboxylase, and prepare a large number of diphosphomevalonate decarboxylase variants. Then, these variants were evaluated in terms of the catalytic activity for isoprene production using 3-hydroxy-3-methylpent-4-enotate as a substrate.

Note that, in the past, the present inventors prepared about 200 amino acid variants of diphosphomevalonate decarboxylase, and evaluated the variants in terms of the catalytic activity for isoprene production using 3-hydroxy-3-methylpent-4-enotate as a substrate. As a result, the present inventors found that a diphosphomevalonate decarboxylase (R74HT209R) in which arginine at position 74 is substituted with histidine and threonine at position 209 is substituted with arginine exhibited by far the highest catalytic activity for isoprene production among the many, about 200 variants (e.g., exhibited a catalytic activity nearly 70 times that of wild-type diphosphomevalonate decarboxylase) (see NPL 1).

<Preparation of Plasmid Vector>

First, in order to efficiently express Saccharomyces cerevisiae-derived MVD (scMVD, a protein comprising the amino acid sequence specified in SEQ ID NO: 2) in Escherichia coli, a wild-type nucleotide sequence (the nucleotide sequence specified in SEQ ID NO: 1) encoding the MVD was modified by taking the codon use frequency in Escherichia coli into consideration. Then, a DNA comprising the modified nucleotide sequence (the nucleotide sequence specified in SEQ ID NO: 3) was chemically synthesized according to a conventional method. Subsequently, the DNA thus prepared was inserted into a multiple cloning site (between NdeI and BamHI recognition sites) of pET-22b(+) vector (manufactured by Novagen Inc.). Thus, a plasmid vector (scMVD vector) was prepared which was capable of expressing the wild-type scMVD in Escherichia coli, the wild-type scMVD having a polyhistidine tag fused at the N-terminus thereof.

Next, to introduce a mutation involving amino acid substitution into each position of the scMVD, primers encoding amino acid sequences having mutations introduced therein were designed and synthesized. Then, using the scMVD vector as a template as well as these primers and a site-directed mutagenesis kit (product name: site-Direct Mutagenesis Kit, manufactured by Agilent Technologies, Inc.), plasmid vectors were prepared which were capable of expressing scMVDs in Escherichia coli in accordance with the protocol attached to the kit, the scMVDs each having the mutation introduced therein and the polyhistidine tag fused at the N-terminus thereof.

<Preparation of Enzyme Solution>

Each of the plasmid vectors prepared as described above was introduced into Escherichia coli (BL21) by a heat shock method, and transformants were prepared which were capable of expressing the wild-type scMVD or the scMVD variants. Then, each of these transformants was cultured overnight in an LB medium supplemented with 0.4 mM IPTG and ampicillin. After the culturing, the transformant was collected by centrifugation, and lysed by adding a DNase I-supplemented protein extraction reagent (product name: B-PER, manufactured by Thermo Fisher Scientific Inc.). Each of lysates obtained in this manner was centrifuged, and a supernatant thus obtained was added to a polyhistidine purification column (product name: TALON (registered trademark) column, manufactured by Clontech Laboratories, Inc.). Then, an elution solution (20 mM Tris-HCl (pH 7.4), 300 mM NaCl, and 150 mM imidazole) was added to each column to elute the scMVD to which the polyhistidine tag was fused. Subsequently, each elution solution was dialyzed with a buffer (20 mM Tris-HCl (pH 7.4) and 100 mM NaCl), and then concentrated with an ultrafiltration spin column (product name: Amicon Ultra, manufactured by Millipore Corporation). Thus, an enzyme solution was prepared. Moreover, the concentration of the enzyme (the scMVD or each of the variants to which the polyhistidine tag was fused) in the solution prepared as described above was measured using a protein quantification kit (product name: BCA Assay Kit, manufactured by TaKaRa Bio Inc.) in accordance with the protocol attached thereto.

<Enzymatic Activity Measurement 1>

Each enzymatic activity in isoprene synthesis using 3-hydroxy-3-methylpent-4-enotate as a substrate was measured as follows. First, 0.5 mM 3-hydroxy-3-methylpent-4-enotate and 5 mM ATP were added to a buffer (50 mM Tris-HCl (pH 7.5), 10 mM $MgCl_2$, and 100 mM KCl). Then, 2.5 ml of this reaction solution and 0.5 mg of the enzyme were added to a 10-ml vial for gas chromatography mass spectrometry (GC-MS). Immediately after that, the cap of the vial was closed to start the enzyme reaction. The enzyme reaction was allowed to proceed at 37° C. Then, 72 hours after the start of the reaction, the vial was heated at 50° C. for 30 minutes for sample equilibration and then the amount of isoprene produced in the head space of the vial was measured by GC-MS (product name: GCMS-QP2010 Ultra, manufactured by Shimadzu Corporation). Subsequently, the measured value obtained for each of the variants was converted by calculation to a value relative to the measured value for the R74HT209R used as a reference (1). Some of the results obtained are presented in FIG. 1.

As presented in FIG. 1, it was found out that the diphosphomevalonate decarboxylase (S153XT209X) in which the serine at position 153 and the threonine at position 209 in the diphosphomevalonate decarboxylase are each substituted with a different amino acid has very high catalytic activity for isoprene production.

Specifically, it was possible to newly obtain a variant having about four times or higher catalytic activity than that of R74HT209R, which had been obtained in the past as an only variant, among the approximately 200 variants, with a very high catalytic activity for isoprene production.

Note that, as presented in FIG. 1, it was impossible to obtain a variant having a high catalytic activity such as R74HT209R, even when only the serine at position 153 of diphosphomevalonate decarboxylase was substituted with a different amino acid.

Moreover, a triple amino acid variant was also prepared in which the glycine at position 152 in the aforementioned S153XT209X was also further substituted with a different amino acid, and the catalytic activity for isoprene production was evaluated. As a result, as presented in FIG. 1, it has been revealed that, as a consequence of further amino acid substitution, the catalytic activity for isoprene production is improved about 1.3 times as compared with S153XT209X.

Figure 2:
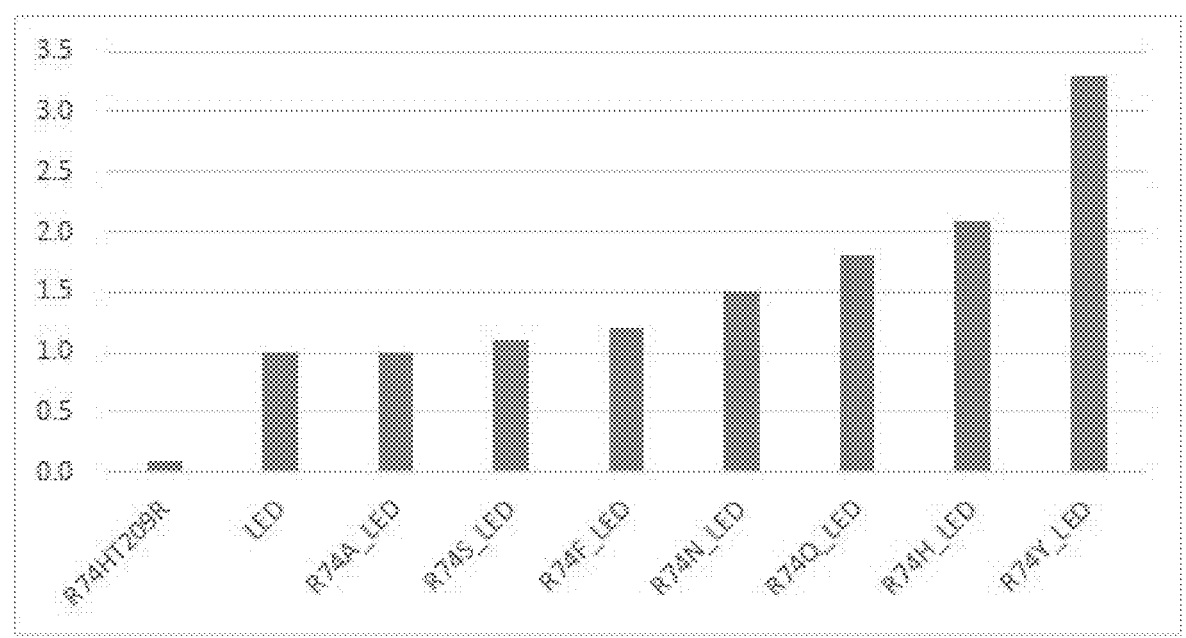
FIG. 2 is a graph about a triple amino acid variant (indicated as "LED" in the figure) of diphosphomevalonate decarboxylase in which glycine at position 152, serine at position 153, and threonine at position 209 are substituted with leucine, glutamic acid, and aspartic acid, respectively and about a quadruple amino acid variant (indicated as "R74X_LED" in the figure) in which an amino acid at position 74 is further substituted with a different amino acid, the graph presenting results of analyzing an enzymatic activity for isoprene production using 3-hydroxy-3-methylpent-4-enotate as a substrate. Note that the vertical axis indicates an amount of isoprene produced by each amino acid variant, the amount being expressed as a relative value calculated by using the amount in the triple amino acid variant as a reference (1). Also, the graph presents, as a control, a relative value of the amount of isoprene produced by R74HT209R.

Furthermore, a quadruple amino acid variant was also prepared in which the arginine at position 74 was further substituted with a different amino acid in the aforementioned triple amino acid variant (the glycine at position 152, the serine at position 153, and the threonine at position 209 were substituted with leucine, glutamic acid, and aspartic acid, respectively; G152LS153ET209D), and the catalytic activity for isoprene production was evaluated. FIG. 2 presents the obtained results.

Note that FIG. 2 presents the results of calculating the relative value of the measured value of GC-MS in each variant using the measured value in G152LS153ET209D as a reference (1). In addition, FIG. 2 also presents the measured value for R74HT209R.

As presented in FIG. 2, it has been revealed that, as a consequence of further amino acid substitution at position 74, the catalytic activity for isoprene production can be further improved as compared with the 6 triple amino acid variant. In particular, substitution of the arginine at position 74 with asparagine, glutamine, histidine, or tyrosine improved the catalytic activity at least 1.5 times and at most more than 3 times as compared with the triple amino acid variant.

Note that, although not presented in the figures and tables, the activity of quadruple variants was similarly evaluated in which the arginine at position 74 was substituted with amino acids other than asparagine, glutamine, histidine, and tyrosine. As a result, it was 16 found that all of them exhibited a higher catalytic activity than that of R74HT209R.

<Enzymatic Activity Measurement 2>

Next, the present inventors verified that the above-described variant is also usable in the production of an olefin compound other than isoprene. To be more specific, each enzymatic activity in isobutene synthesis (reaction represented by the following equation) using β-hydroxyisovaleric acid as a substrate was evaluated as follows.

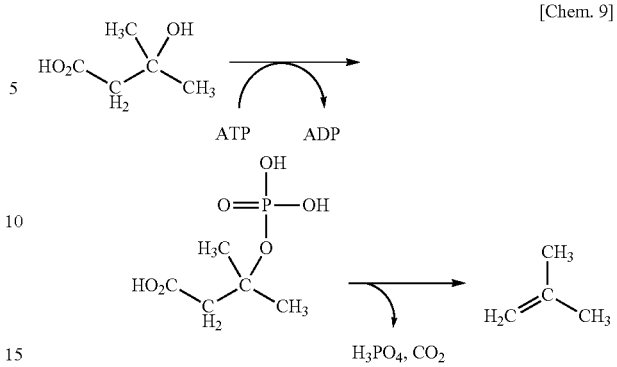

[Chem. 9]

Figure 3:
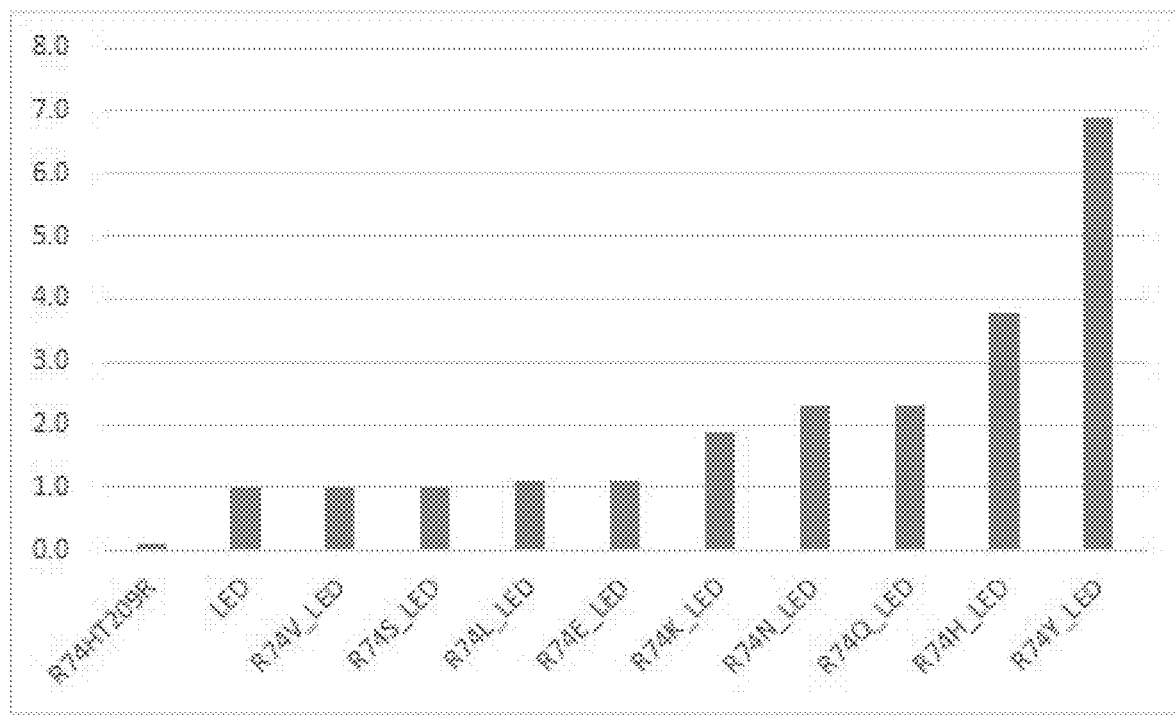
FIG. 3 is a graph about the triple amino acid variant (indicated as "LED" in the figure) and the quadruple amino acid variant (indicated as "R74X_LED" in the figure), the graph presenting results of analyzing an enzymatic activity for isobutene production using β-hydroxyisovaleric acid as a substrate. Note that the vertical axis indicates an amount of isobutene produced by each amino acid variant, the amount being expressed as a relative value calculated by using the amount in the triple amino acid variant as a reference (1). Also, the graph presents, as a control, a relative value of the amount of isobutene produced by R74HT209R.

First, 0.5 mM β-hydroxyisovaleric acid (manufactured by Tokyo Chemical Industry Co., Ltd., product code: H0701) and 5 mM ATP were added to a buffer (50 mM Tris-HCl (pH 7.5), 10 mM $MgCl_2$, and 100 mM KCl). Then, 2.5 ml of this reaction liquid and 10 mg of the enzyme were added to a 10-ml vial for GC-MS. Immediately after that, the cap of the vial was closed to start the enzyme reaction. The enzymatic reaction was allowed to proceed at 37° C. Several days (approximately 2 days) after the reaction was started, the vial was heated at 50° C. for 30 minutes for the sample equilibration, and then the amount of isobutene produced in the head space of the vial was measured by GC-MS (product name: GCMS-QP2010 Ultra, manufactured by Shimadzu Corporation). FIG. 3 presents the obtained results.

Note that FIG. 3 presents the results of calculating the relative value of the measured value of GC-MS in each variant using the measured value in G152LS153ET209D as a reference (1). In addition, FIG. 3 also presents the measured value for R74HT209R.

As presented in FIG. 3, it has been found that the triple amino acid variant also has a high catalytic activity for isobutene production as compared with R74HT209R as in the case of isoprene production. In addition, it has also been found that, as a consequence of further amino acid substitution at position 74, the high catalytic activity can be further improved as compared with the triple amino acid variant. In particular, substitution of the arginine at position 74 with asparagine, glutamine, histidine, or tyrosine improved the catalytic activity in the isobutene production at least twice and at most about 7 times as compared with the triple amino acid variant.

Note that, although not presented in the figures and tables, the activity of quadruple variants was similarly evaluated in which the arginine at position 74 was substituted with amino acids other than asparagine, glutamine, histidine, and tyrosine. As a result, it was found that all of them exhibited a higher catalytic activity than that of R74HT209R.

INDUSTRIAL APPLICABILITY

As has been described above, the present invention provides an enzyme enabling olefin compound production with a high productivity, and a method for producing an olefin compound by using the enzyme. Moreover, since olefin compounds can be produced by not chemical synthesis but biosynthesis, the present invention is more environmentally friendly. Thus, the present invention is very useful in the production of raw materials for various synthetic polymers such as synthetic rubbers.

[Sequence Listing Free Text]
SEQ ID NO: 3
<223> Sequence codon-optimized for E. coli expression
[Sequence Listing] IBPF17-543WO-J(seq)fin.txt

SEQUENCE LISTING

<160> NUMBER OF SEQ ID NOS: 3

<210> SEQ ID NO 1
<211> LENGTH: 1191
<212> TYPE: DNA
<213> ORGANISM: Saccharomyces cerevisiae
<220> FEATURE:
<221> NAME/KEY: CDS
<222> LOCATION: (1)..(1191)

<400> SEQUENCE: 1

```
atg acc gtt tac aca gca tcc gtt acc gca ccc gtc aac atc gca acc      48
Met Thr Val Tyr Thr Ala Ser Val Thr Ala Pro Val Asn Ile Ala Thr
1               5                   10                  15 ctt aag tat tgg ggg aaa agg gac acg aag ttg aat ctg ccc acc aat      96
Leu Lys Tyr Trp Gly Lys Arg Asp Thr Lys Leu Asn Leu Pro Thr Asn
                20                  25                  30 tcg tcc ata tca gtg act tta tcg caa gat gac ctc aga acg ttg acc     144
Ser Ser Ile Ser Val Thr Leu Ser Gln Asp Asp Leu Arg Thr Leu Thr
            35                  40                  45 tct gcg gct act gca cct gag ttt gaa cgc gac act ttg tgg tta aat     192
Ser Ala Ala Thr Ala Pro Glu Phe Glu Arg Asp Thr Leu Trp Leu Asn
        50                  55                  60 gga gaa cca cac agc atc gac aat gaa aga act caa aat tgt ctg cgc     240
Gly Glu Pro His Ser Ile Asp Asn Glu Arg Thr Gln Asn Cys Leu Arg
65                  70                  75                  80 gac cta cgc caa tta aga aag gaa atg gaa tcg aag gac gcc tca ttg     288
Asp Leu Arg Gln Leu Arg Lys Glu Met Glu Ser Lys Asp Ala Ser Leu
                85                  90                  95 ccc aca tta tct caa tgg aaa ctc cac att gtc tcc gaa aat aac ttt     336
Pro Thr Leu Ser Gln Trp Lys Leu His Ile Val Ser Glu Asn Asn Phe
                100                 105                 110 cct aca gca gct ggt tta gct tcc tcc gct gct ggc ttt gct gca ttg     384
Pro Thr Ala Ala Gly Leu Ala Ser Ser Ala Ala Gly Phe Ala Ala Leu
            115                 120                 125 gtc tct gca att gct aag tta tac caa tta cca cag tca act tca gaa     432
Val Ser Ala Ile Ala Lys Leu Tyr Gln Leu Pro Gln Ser Thr Ser Glu
        130                 135                 140 ata tct aga ata gca aga aag ggg tct ggt tca gct tgt aga tcg ttg     480
Ile Ser Arg Ile Ala Arg Lys Gly Ser Gly Ser Ala Cys Arg Ser Leu
145                 150                 155                 160 ttt ggc gga tac gtg gcc tgg gaa atg gga aaa gct gaa gat ggt cat     528
Phe Gly Gly Tyr Val Ala Trp Glu Met Gly Lys Ala Glu Asp Gly His
                165                 170                 175 gat tcc atg gca gta caa atc gca gac agc tct gac tgg cct cag atg     576
Asp Ser Met Ala Val Gln Ile Ala Asp Ser Ser Asp Trp Pro Gln Met
            180                 185                 190 aaa gct tgt gtc cta gtt gtc agc gat att aaa aag gat gtg agt tcc     624
Lys Ala Cys Val Leu Val Val Ser Asp Ile Lys Lys Asp Val Ser Ser
        195                 200                 205 act cag ggt atg caa ttg acc gtg gca acc tcc gaa cta ttt aaa gaa     672
Thr Gln Gly Met Gln Leu Thr Val Ala Thr Ser Glu Leu Phe Lys Glu
    210                 215                 220 aga att gaa cat gtc gta cca aag aga ttt gaa gtc atg cgt aaa gcc     720
Arg Ile Glu His Val Val Pro Lys Arg Phe Glu Val Met Arg Lys Ala
225                 230                 235                 240
```

```
att gtt gaa aaa gat ttc gcc acc ttt gca aag gaa aca atg atg gat      768
Ile Val Glu Lys Asp Phe Ala Thr Phe Ala Lys Glu Thr Met Met Asp
            245                 250                 255 tcc aac tct ttc cat gcc aca tgt ttg gac tct ttc cct cca ata ttc      816
Ser Asn Ser Phe His Ala Thr Cys Leu Asp Ser Phe Pro Pro Ile Phe
            260                 265                 270 tac atg aat gac act tcc aag cgt atc atc agt tgg tgc cac acc att      864
Tyr Met Asn Asp Thr Ser Lys Arg Ile Ile Ser Trp Cys His Thr Ile
            275                 280                 285 aat cag ttt tac gga gaa aca atc gtt gca tac acg ttt gat gca ggt      912
Asn Gln Phe Tyr Gly Glu Thr Ile Val Ala Tyr Thr Phe Asp Ala Gly
            290                 295                 300 cca aat gct gtg ttg tac tac tta gct gaa aat gag tcg aaa ctc ttt      960
Pro Asn Ala Val Leu Tyr Tyr Leu Ala Glu Asn Glu Ser Lys Leu Phe
305                 310                 315                 320 gca ttt atc tat aaa ttg ttt ggc tct gtt cct gga tgg gac aag aaa     1008
Ala Phe Ile Tyr Lys Leu Phe Gly Ser Val Pro Gly Trp Asp Lys Lys
                325                 330                 335 ttt act act gag cag ctt gag gct ttc aac cat caa ttt gaa tca tct     1056
Phe Thr Thr Glu Gln Leu Glu Ala Phe Asn His Gln Phe Glu Ser Ser
                340                 345                 350 aac ttt act gca cgt gaa ttg gat ctt gag ttg caa aag gat gtt gcc     1104
Asn Phe Thr Ala Arg Glu Leu Asp Leu Glu Leu Gln Lys Asp Val Ala
                355                 360                 365 aga gtg att tta act caa gtc ggt tca ggc cca caa gaa aca aac gaa     1152
Arg Val Ile Leu Thr Gln Val Gly Ser Gly Pro Gln Glu Thr Asn Glu
370                 375                 380 tct ttg att gac gca aag act ggt cta cca aag gaa taa                 1191
Ser Leu Ile Asp Ala Lys Thr Gly Leu Pro Lys Glu
385                 390                 395

<210> SEQ ID NO 2
<211> LENGTH: 396
<212> TYPE: PRT
<213> ORGANISM: Saccharomyces cerevisiae

<400> SEQUENCE: 2

Met Thr Val Tyr Thr Ala Ser Val Thr Ala Pro Val Asn Ile Ala Thr
1               5                   10                  15

Leu Lys Tyr Trp Gly Lys Arg Asp Thr Lys Leu Asn Leu Pro Thr Asn
                20                  25                  30

Ser Ser Ile Ser Val Thr Leu Ser Gln Asp Asp Leu Arg Thr Leu Thr
            35                  40                  45

Ser Ala Ala Thr Ala Pro Glu Phe Glu Arg Asp Thr Leu Trp Leu Asn
        50                  55                  60

Gly Glu Pro His Ser Ile Asp Asn Glu Arg Thr Gln Asn Cys Leu Arg
65                  70                  75                  80

Asp Leu Arg Gln Leu Arg Lys Glu Met Glu Ser Lys Asp Ala Ser Leu
                85                  90                  95

Pro Thr Leu Ser Gln Trp Lys Leu His Ile Val Ser Glu Asn Asn Phe
            100                 105                 110

Pro Thr Ala Ala Gly Leu Ala Ser Ser Ala Gly Phe Ala Ala Leu
        115                 120                 125

Val Ser Ala Ile Ala Lys Leu Tyr Gln Leu Pro Gln Ser Thr Ser Glu
    130                 135                 140

Ile Ser Arg Ile Ala Arg Lys Gly Ser Gly Ser Ala Cys Arg Ser Leu
145                 150                 155                 160

Phe Gly Gly Tyr Val Ala Trp Glu Met Gly Lys Ala Glu Asp Gly His
```

-continued

```
                  165                 170                 175

Asp Ser Met Ala Val Gln Ile Ala Asp Ser Ser Asp Trp Pro Gln Met
                180                 185                 190

Lys Ala Cys Val Leu Val Val Ser Asp Ile Lys Lys Asp Val Ser Ser
            195                 200                 205

Thr Gln Gly Met Gln Leu Thr Val Ala Thr Ser Glu Leu Phe Lys Glu
        210                 215                 220

Arg Ile Glu His Val Val Pro Lys Arg Phe Glu Val Met Arg Lys Ala
225                 230                 235                 240

Ile Val Glu Lys Asp Phe Ala Thr Phe Ala Lys Glu Thr Met Met Asp
                245                 250                 255

Ser Asn Ser Phe His Ala Thr Cys Leu Asp Ser Phe Pro Pro Ile Phe
            260                 265                 270

Tyr Met Asn Asp Thr Ser Lys Arg Ile Ile Ser Trp Cys His Thr Ile
        275                 280                 285

Asn Gln Phe Tyr Gly Glu Thr Ile Val Ala Tyr Thr Phe Asp Ala Gly
    290                 295                 300

Pro Asn Ala Val Leu Tyr Tyr Leu Ala Glu Asn Glu Ser Lys Leu Phe
305                 310                 315                 320

Ala Phe Ile Tyr Lys Leu Phe Gly Ser Val Pro Gly Trp Asp Lys Lys
                325                 330                 335

Phe Thr Thr Glu Gln Leu Glu Ala Phe Asn His Gln Phe Glu Ser Ser
            340                 345                 350

Asn Phe Thr Ala Arg Glu Leu Asp Leu Glu Leu Gln Lys Asp Val Ala
        355                 360                 365

Arg Val Ile Leu Thr Gln Val Gly Ser Gly Pro Gln Glu Thr Asn Glu
    370                 375                 380

Ser Leu Ile Asp Ala Lys Thr Gly Leu Pro Lys Glu
385                 390                 395
```

```
<210> SEQ ID NO 3
<211> LENGTH: 1191
<212> TYPE: DNA
<213> ORGANISM: Artificial Sequence
<220> FEATURE:
<223> OTHER INFORMATION: Sequence codon-optimized for E.coli expression
<220> FEATURE:
<221> NAME/KEY: CDS
<222> LOCATION: (1)..(1191)

<400> SEQUENCE: 3
```

```
atg acc gtt tat acc gca agc gtt acc gca ccg gtt aat att gca acc     48
Met Thr Val Tyr Thr Ala Ser Val Thr Ala Pro Val Asn Ile Ala Thr
1               5                   10                  15 ctg aaa tat tgg ggt aaa cgc gat acc aaa ctg aat ctg ccg acc aat     96
Leu Lys Tyr Trp Gly Lys Arg Asp Thr Lys Leu Asn Leu Pro Thr Asn
            20                  25                  30 agc agc att agc gtt acc ctg agc cag gat gat ctg cgt acc ctg acc    144
Ser Ser Ile Ser Val Thr Leu Ser Gln Asp Asp Leu Arg Thr Leu Thr
        35                  40                  45 agc gca gca aca gca ccg gaa ttt gaa cgt gat acc ctg tgg ctg aat    192
Ser Ala Ala Thr Ala Pro Glu Phe Glu Arg Asp Thr Leu Trp Leu Asn
    50                  55                  60 ggt gaa ccg cat agc att gat aat gaa cgt acc cag aat tgt ctg cgt    240
Gly Glu Pro His Ser Ile Asp Asn Glu Arg Thr Gln Asn Cys Leu Arg
65                  70                  75                  80 gat ctg cgc cag ctg cgt aaa gaa atg gaa agc aaa gat gca agc ctg    288
Asp Leu Arg Gln Leu Arg Lys Glu Met Glu Ser Lys Asp Ala Ser Leu
```

|  |  |
|---|---:|
| ccg acc ctg agt cag tgg aaa ctg cat att gtt agc gaa aat aac ttt<br>Pro Thr Leu Ser Gln Trp Lys Leu His Ile Val Ser Glu Asn Asn Phe<br>     100                  105               110 | 336 |
| ccg acc gca gca ggt ctg gca agc agc gca gcc ggt ttt gca gca ctg<br>Pro Thr Ala Ala Gly Leu Ala Ser Ser Ala Ala Gly Phe Ala Ala Leu<br>     115                  120               125 | 384 |
| gtt agc gca att gca aaa ctg tat cag ctg ccg cag agc acc agc gaa<br>Val Ser Ala Ile Ala Lys Leu Tyr Gln Leu Pro Gln Ser Thr Ser Glu<br>130                 135               140 | 432 |
| att agc cgt att gca cgt aaa ggt agc ggt agc gca tgt cgt agc ctg<br>Ile Ser Arg Ile Ala Arg Lys Gly Ser Gly Ser Ala Cys Arg Ser Leu<br>145                 150               155              160 | 480 |
| ttt ggt ggt tat gtt gca tgg gaa atg ggt aaa gcc gaa gat ggt cat<br>Phe Gly Gly Tyr Val Ala Trp Glu Met Gly Lys Ala Glu Asp Gly His<br>                    165               170              175 | 528 |
| gat agc atg gca gtt cag att gca gat agc agc gat tgg cct cag atg<br>Asp Ser Met Ala Val Gln Ile Ala Asp Ser Ser Asp Trp Pro Gln Met<br>     180                  185               190 | 576 |
| aaa gca tgt gtt ctg gtt gtg agc gat atc aaa aaa gat gtt agc agc<br>Lys Ala Cys Val Leu Val Val Ser Asp Ile Lys Lys Asp Val Ser Ser<br>                    195               200              205 | 624 |
| acc cag ggt atg cag ctg acc gtt gca acc agc gaa ctg ttt aaa gaa<br>Thr Gln Gly Met Gln Leu Thr Val Ala Thr Ser Glu Leu Phe Lys Glu<br>     210                  215               220 | 672 |
| cgt att gaa cat gtt gtg ccg aaa cgc ttt gaa gtt atg cgt aaa gcc<br>Arg Ile Glu His Val Val Pro Lys Arg Phe Glu Val Met Arg Lys Ala<br>225                 230               235              240 | 720 |
| att gtc gaa aaa gat ttt gcc acc ttt gca aaa gaa acc atg atg gat<br>Ile Val Glu Lys Asp Phe Ala Thr Phe Ala Lys Glu Thr Met Met Asp<br>                    245               250              255 | 768 |
| agc aat agc ttt cat gca acc tgt ctg gat agc ttt ccg cct atc ttt<br>Ser Asn Ser Phe His Ala Thr Cys Leu Asp Ser Phe Pro Pro Ile Phe<br>     260                  265               270 | 816 |
| tat atg aac gat acc agc aaa cgc att atc agc tgg tgt cat acc atc<br>Tyr Met Asn Asp Thr Ser Lys Arg Ile Ile Ser Trp Cys His Thr Ile<br>                    275               280              285 | 864 |
| aat cag ttt tat ggt gaa acc att gtg gcc tat acc ttt gat gca ggt<br>Asn Gln Phe Tyr Gly Glu Thr Ile Val Ala Tyr Thr Phe Asp Ala Gly<br>     290                  295               300 | 912 |
| ccg aat gca gtt ctg tat tat ctg gca gaa aat gaa agc aaa ctg ttc<br>Pro Asn Ala Val Leu Tyr Tyr Leu Ala Glu Asn Glu Ser Lys Leu Phe<br>305                 310               315              320 | 960 |
| gcc ttc atc tac aaa ctg ttt ggt agc gtt ccg ggt tgg gac aaa aaa<br>Ala Phe Ile Tyr Lys Leu Phe Gly Ser Val Pro Gly Trp Asp Lys Lys<br>                    325               330              335 | 1008 |
| ttc acc acc gaa cag ctg gaa gca ttt aac cat cag ttt gaa agc agc<br>Phe Thr Thr Glu Gln Leu Glu Ala Phe Asn His Gln Phe Glu Ser Ser<br>     340                  345               350 | 1056 |
| aat ttt acc gca cgt gaa ctg gat ctg gaa ctg cag aaa gat gtt gca<br>Asn Phe Thr Ala Arg Glu Leu Asp Leu Glu Leu Gln Lys Asp Val Ala<br>          355                  360               365 | 1104 |
| cgt gtt att ctg acc cag gtg ggt agc ggt ccg caa gaa acc aat gaa<br>Arg Val Ile Leu Thr Gln Val Gly Ser Gly Pro Gln Glu Thr Asn Glu<br>     370                  375               380 | 1152 |
| agc ctg atc gat gca aaa acc ggt ctg ccg aaa gaa tga<br>Ser Leu Ile Asp Ala Lys Thr Gly Leu Pro Lys Glu<br>385                 390               395 | 1191 |

The invention claimed is:

1. A method for producing isoprene or isobutene, the method comprising:
reacting ATP and a substrate compound in the presence of a diphosphomevalonate decarboxylase to produce isoprene or isobutene,
wherein:
the diphosphomevalonate decarboxylase is a protein in which:
serine at position 153 of SEQ ID NO: 2 or serine corresponding to the position is mutated to aspartic acid or glutamic acid,
threonine at position 209 of SEQ ID NO: 2 or threonine corresponding to the position is mutated to aspartic acid, and
the amino acid sequence consists of the amino acid sequence of SEQ ID NO: 2 or an amino acid sequence in which no more than 40 amino acid residues of the amino acid sequence of SEQ ID NO: 2 are substituted, deleted, added, and/or inserted other than at positions 153 and 209,
and
when the method produces isoprene, the substrate compound is 3-hydroxy-3-methylpent-4-enoate and when the method produces isobutene, the substrate compound is (β-hydroxyisovaleric acid.

2. The production method according to claim 1, wherein reacting ATP and the substrate compound in the presence of the diphosphomevalonate decarboxylase is performed by culturing a host cell comprising:
a DNA encoding the diphosphomevalonate decarboxylase, or
a vector comprising the DNA.

3. The production method according to claim 1, wherein in the diphosphomevalonate decarboxylase, glycine at position 152 of SEQ ID NO: 2 or glycine corresponding to the position is mutated to a different amino acid.

4. The production method according to claim 3, wherein the different amino acid mutated from the glycine at position 152 of SEQ ID NO: 2 or the glycine corresponding to the position is leucine.

5. The production method according to claim 1, wherein the method produces isoprene.

* * * * *